(12) United States Patent
Dubois et al.

(10) Patent No.: US 8,530,697 B2
(45) Date of Patent: Sep. 10, 2013

(54) METHOD FOR THE REACTIVE VAPORIZATION OF GLYCEROL

(75) Inventors: Jean-Luc Dubois, Millery (FR); Grégory Patience, Québec (CA)

(73) Assignee: Arkema France, Colombes (FR)

( * ) Notice: Subject to any disclaimer, the term of this patent is extended or adjusted under 35 U.S.C. 154(b) by 416 days.

(21) Appl. No.: 12/676,782

(22) PCT Filed: Sep. 5, 2008

(86) PCT No.: PCT/FR2008/051585
§ 371 (c)(1),
(2), (4) Date: Sep. 8, 2010

(87) PCT Pub. No.: WO2009/044051
PCT Pub. Date: Apr. 9, 2009

(65) Prior Publication Data
US 2011/0028760 A1    Feb. 3, 2011

(30) Foreign Application Priority Data
Sep. 6, 2007    (FR) ..................... 07 57396

(51) Int. Cl.
*C07C 51/00*    (2006.01)
*C07C 45/00*    (2006.01)

(52) U.S. Cl.
USPC ......................... 562/538; 568/449

(58) Field of Classification Search
USPC ......................... 562/538; 568/449
See application file for complete search history.

(56) References Cited

U.S. PATENT DOCUMENTS

| | | | |
|---|---|---|---|
| 4,477,492 A | 10/1984 | Bergna et al. | |
| 4,677,084 A | 6/1987 | Bergna | |
| 4,769,477 A | 9/1988 | Bergna | |
| 4,849,539 A | 7/1989 | Bergna | |
| 5,302,566 A | 4/1994 | Schwartz | |
| 5,387,720 A | 2/1995 | Neher et al. | |
| 6,107,238 A | 8/2000 | Contractor et al. | |
| 6,281,384 B1 | 8/2001 | Contracter et al. | |
| 6,310,240 B1 | 10/2001 | Contractor et al. | |
| 6,362,128 B1 | 3/2002 | Schwartz | |

(Continued)

FOREIGN PATENT DOCUMENTS

| | | |
|---|---|---|
| EP | 0697247 | 2/1996 |
| FR | 2826959 | 1/2003 |

(Continued)

OTHER PUBLICATIONS

Anderson, et al; "*Glycerine Recovery from Spent Lyes and Sweetwater*", Crown Iron Works Company; Chapter 6; pp. 172-207, Oct. 1994.

(Continued)

*Primary Examiner* — Taylor Victor Oh
(74) *Attorney, Agent, or Firm* — Hunton & Williams LLP

(57) ABSTRACT

The subject of the present invention is a method for the reactive vaporization of aqueous solutions of glycerol in a fluidized bed containing a reactive solid. The method of the invention makes it possible to simultaneously vaporize an aqueous solution of glycerol, to remove the impurities that are present in this solution or that are generated during the evaporation, and to carry out the dehydration reaction of the glycerol to acrolein and/or the oxydehydration reaction of the glycerol to acrylic acid.

8 Claims, 1 Drawing Sheet

(56) References Cited

U.S. PATENT DOCUMENTS

| | | |
|---|---|---|
| 6,437,193 B1 | 8/2002 | Contractor et al. |
| 6,667,419 B1 | 12/2003 | Matsumoto et al. |
| 6,878,668 B1 | 4/2005 | Schwartz et al. |
| 7,396,962 B1 | 7/2008 | Dubois et al. |
| 7,655,818 B2 | 2/2010 | Dubois et al. |
| 2008/0146852 A1* | 6/2008 | Dubois et al. ............ 568/449 |
| 2008/0183013 A1* | 7/2008 | Dubois et al. ............ 562/538 |
| 2008/0319233 A1 | 12/2008 | Dubois |
| 2009/0018362 A1 | 1/2009 | Dubois et al. |

FOREIGN PATENT DOCUMENTS

| | | |
|---|---|---|
| FR | 2903620 | 1/2008 |
| FR | 2912742 | 8/2008 |
| FR | 2913974 | 9/2008 |
| WO | WO 9726313 | 7/1997 |
| WO | WO 9903809 | 1/1999 |

OTHER PUBLICATIONS

D'Souza; "*The Importance of Glycerol in the Fatty Acid Industry*"; Am. Oil Chemists' Soc. Nov. 1979; vol. 56, p. 812A.

Schaffner; "*Electrodialysis of Crude Glycerin Recovered After Esterification of Colza Oil*"; The British Library—"The world's knowledge"; pp. 629-633.

Taanabe et al; "*Studies in Surface Science and Catalysis*", vol. 51, 1989, Chapters 1 and 2.

* cited by examiner

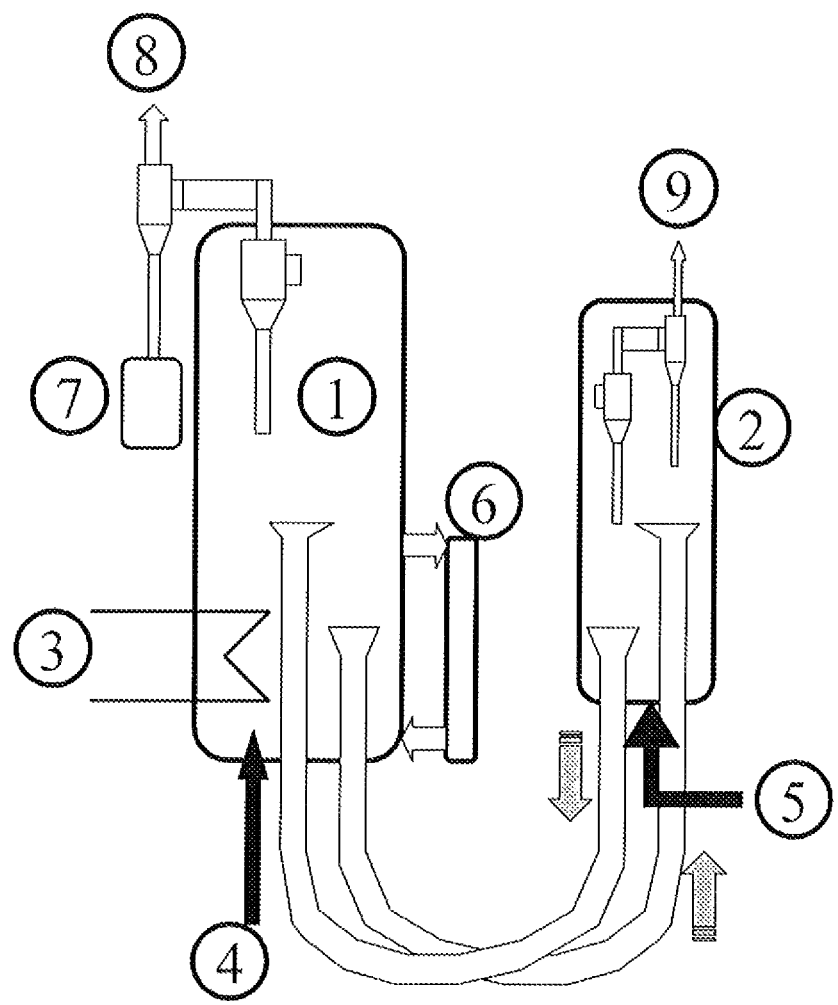

METHOD FOR THE REACTIVE VAPORIZATION OF GLYCEROL

CROSS-REFERENCE TO RELATED APPLICATIONS

This application is the U.S. National Phase of International Application No. PCT/FR2008/051585, filed Sep. 5, 2008, which claims the benefit of French Application No. FR 0757396, filed Sep. 6, 2007, the disclosure of each of which is incorporated herein by reference in its entirety.

FIELD OF THE INVENTION

One subject of the present invention is a method of vaporizing aqueous solutions of glycerol in a fluidized bed containing a reactive solid, that makes it possible to simultaneously vaporize the aqueous solution of glycerol, remove the impurities present in this solution or that are generated during the evaporation and carry out the dehydration reaction of glycerol to acrolein and/or the oxydehydration reaction of glycerol to acrylic acid.

BACKGROUND

Glycerol is a chemical, 1,2,3-propanetriol, which may be obtained either by chemical synthesis from propylene, or as a by-product formed during the methanolysis of vegetable oils.

The methanolysis of vegetable oils may be carried out according to various processes, in particular by using a homogeneous catalyst such as sodium hydroxide or sodium methylate in solution in methanol, or by using a heterogeneous catalyst. Reference may be made, on this subject, to the article by D. Ballerini et al. in L'Actualité Chimique of November-December 2002.

The methanolysis of vegetable oils results, on the one hand, in methyl esters, and on the other hand in glycerol. Methyl esters are used in particular as fuels or combustibles in diesel fuel and domestic fuel. With the development of fuels of renewable origins, and especially of vegetable oil methyl esters (VOMEs), the production of glycerol in accordance with this production method increases greatly, glycerol representing around 10% by weight of the oil converted.

Glycerol derived from vegetable oils is a natural product of renewable origin which is thus increasingly available. In the current context of the novel concept of green chemistry, and more generally of sustainable development, it is becoming increasingly advantageous to utilize this product.

However, the methods for producing VOMEs result in a glycerol that is more or less pure and more or less dilute in water. Generally, it is these more or less pure aqueous solutions of glycerol that are known as glycerin, according to the definition adopted by "The Soap and Detergent Association" (Soaps and Detergents: A theoretical and Practical Review, Miami Beach Fla., Oct. 12-14, 1994, chapter 6 pp. 172-206. Ed: L Spitz, AOCS Press, Champaign). The methanolysis of vegetable oils is carried out in a basic medium, for example with sodium hydroxide. The effluent is neutralized with hydrochloric acid or with sulfuric acid. These treatments leave impurities in the glycerin. By way of illustration, the following table gives the typical analyses of various glycerins produced at various industrial sites:

|  | Diester Industries | Diester Industries | Diester Industries |
|---|---|---|---|
| Site | Robbe | Saipol | Marl (RFA) |
| Production | 10 kt/year | 25 kt/year | 15 kt/year |
| Glycerol | 65 wt % | 93 wt % | 85 wt % |
| Water | 31 wt % | 4 wt % | 10 wt % |
| NGOM | 1 wt % | 1 wt % | 0.5 wt % |
| Ash | 3 wt % $Na_2SO_4$ | 2.5 wt % NaCl | 4.5 wt % NaCl |
| Methanol | 0.3 wt % | 0.2 wt % | <0.01 wt % |

NGOM: non-glycerin organic matter: fatty acids, ester, other

Crude glycerin generally has a composition of the order of 88% glycerol, 9-10% water and 2-3% impurities. In particular, it may contain impurities such as basic salts (for example of sodium or of potassium), non-glycerin organic compounds, methanol or residues of vegetable oils. In certain applications of glycerol, the presence of these impurities is particularly prejudicial for the reactions carried out or for the quality of the finished products. For example, in the case of the production of acrolein, the presence of sodium or potassium salts is prejudicial for the catalytic dehydration reaction of glycerol to acrolein, as these salts are capable of poisoning the acid sites of the catalysts used.

Consequently, the aqueous solutions of crude glycerol or glycerin generally require a pretreatment before use, or a purification treatment in order to envisage novel applications.

Furthermore, it is often necessary not only to remove the impurities that are undesirable for the envisaged application, but also to concentrate the aqueous solution, or even to vaporize the aqueous solution, since certain industrial processes use glycerol in vapor form. These operations are tricky as it is known that glycerol may decompose, in particular to acrolein, or result in polymers such as polyglycerol.

Various technologies for purifying glycerol have been described in the literature. Specifically, it is a product that has more than 1500 different applications, all requiring particular qualities, in particular there is a "Pharmacopeia" grade that requires a high purity of the glycerol.

Among the methods used or studied for the purification and evaporation of glycerol, mention will especially be made of those that are described by G. B. D'Souza, in J. Am. Oil Chemists' Soc. November 1979 (Vol 56) 812A, by Steinberner U et al., in Fat. Sci. Technol. (1987), 89 Jahrgang No. 8, pp. 297-303, and by Anderson D. D. et al. in Soaps and Detergents: A theoretical and Practical Review, Miami Beach Fla., Oct. 12-14, 1994, chapter 6, pp. 172-206. Ed: L Spitz, AOCS Press, Champaign.

The treatments of crude glycerol solutions proposed target the removal of the dissolved salts and of the organic impurities resulting from fatty substances, the removal of the color, an increase in the glycerol content, or the vaporization of the glycerol, depending on the final application envisaged.

In particular, in order to achieve these objectives, an evaporation, a distillation, a treatment with lime (in order to neutralize the residual fatty acids) followed by a filtration, an ion exchange or ion exclusion treatment, a separation by reverse osmosis or an electrodialysis may be carried out.

Multiple-effect evaporators are, for example, used for concentrating dilute solutions of glycerol. With a triple-effect evaporator, it is thus possible to evaporate 2.4 kg of water with 1 kg of steam.

Distillation is one of the techniques used for concentrating and purifying glycerin. As glycerol begins to decompose at around 202° C., i.e. well below its boiling point (293° C.), it is necessary to distil glycerin in several steps using reduced pressure. In certain cases, the distillation is carried out via batch operations, until the salts and the non-volatile compounds have accumulated sufficiently in the vessel. The operation is then stopped and the impurities are discharged from the vessel before restarting the distillation. The evaporation is carried out under vacuum, and the partial condensation of glycerol (which will condense before water) at the outlet of the unit makes it possible to directly obtain a concentrated glycerol. Typically, pressures of 10 mmHg are used, for a temperature of 160-165° C., which gives low partial pressures of glycerol in the vapor phase.

The distilled glycerin may still contain colored compounds. It is sometimes necessary to decolorize the glycerin for pharmaceutical and food applications. Typically activated carbon is added to the glycerin in order to decolorize it.

The purification of glycerin by ion exclusion has also been developed and uses ion resins in order to separate the ionic salts that are soluble in aqueous solution from non-ionic compounds such as glycerol. This is a technique which avoids the consumption of heat and of chemical regenerants, and which makes it possible to purify highly contaminated streams such as crude glycerin, using only water as a chemical regenerant.

Aqueous solutions of glycerol that are weakly contaminated by salts may be exchanged simply over acid and basic resins. The thus purified glycerol solutions may then be concentrated by evaporation.

The technique of reverse osmosis, based on a separation through a semi-permeable membrane by applying a pressure has been proposed for the concentration of particularly dilute glycerol streams.

Solutions of glycerin and of sodium hydroxide in methanol obtained after transesterification of rapeseed oil have been demineralized by membrane electrodialysis to produce pure glycerin. This technique is described in the reference: Schaffner, F. et al., Proc.—World Filtr. Congr. 7th, 1996, Volume 2, 629-633.

In the methods proposed for evaporating aqueous solutions of glycerol, the control of the temperature is very critical as certain undesirable reactions may take place, such as the formation of nitrogen-containing compounds by a degradation of protein matter present in the glycerin, the formation of a volatile glycerin ester by reaction with soaps of low molar mass, the formation of polyglycerol, the formation of acrolein which contributes to the odors of the final product. It is therefore important to limit the residence time of the glycerin at high temperature, and also this temperature. The evaporation processes used conventionally do not therefore make it possible to have high partial pressures of glycerol in the vapor phase. Furthermore, it is often necessary to combine several treatments in order to obtain the glycerol with a purity and at a concentration that are suitable for the envisaged application.

In patent application FR 2 913 974, the Applicant Company describes a single-step process that makes it possible to vaporize an aqueous solution of glycerol and to simultaneously remove the impurities present in the solution or that are generated during the evaporation. This process consists in vaporizing the aqueous solution of glycerol in contact with a fluidized bed containing an inert solid maintained at a sufficient temperature to allow the instantaneous vaporization of glycerol and of water. The impurities present in the aqueous solution are simultaneously removed, since the fluidized bed technique makes it possible to continuously draw off a portion of the solid in order to regenerate it ex situ. The glycerol vapors obtained according to this process can then be used directly in a downstream process that employs glycerol in gas form, especially the processes for producing acrolein or acrylic acid described, for example, in documents WO 06/087083, WO 06/087084, WO 06/114506, WO 07/090,990 and WO 07/090,991, or a process for producing acrylonitrile as described in Patent Application FR 2 912 742.

The production of acrolein and/or acrylic acid from glycerol in a gas-phase process, especially according to the aforementioned processes, requires the use of a prior step of vaporization of the glycerol, a step which may prove costly when the glycerol is used in the form of a dilute aqueous solution. Generally, the aqueous solution of glycerol, having undergone, where appropriate, a purification pretreatment according to one of the methods described previously, is vaporized in a heated chamber before passing over a catalyst suitable for the envisaged reaction, in a fixed bed reactor, fluidized bed reactor, circulating fluidized bed reactor or in a plate heat exchanger reactor.

SUMMARY OF THE INVENTION

The Applicant Company has now surprisingly discovered that it is possible to simultaneously vaporize an aqueous solution of glycerol, remove the impurities present in this solution or that are generated during the evaporation, and carry out the dehydration reaction of glycerol to acrolein and/or the oxydehydration reaction of glycerol to acrylic acid. Such a process makes it possible to minimize the energy costs for the production of acrolein and/or of acrylic acid starting from aqueous solutions of glycerol and constitutes a single-step process used in a simplified installation.

One subject of the present invention is therefore a process for the reactive vaporization of aqueous solutions of glycerol (or glycerin) in a fluidized bed containing a reactive solid.

According to the process of the invention, the aqueous glycerol solution is injected directly into a fluidized bed containing a reactive solid maintained at a sufficient temperature to allow the instantaneous vaporization of the glycerol and of water, and also the reaction of the glycerol on the reactive solid.

The concentration of the aqueous glycerol solution may vary to a large extent, for example from 20 to 99% by weight of glycerol, preferably solutions are used that comprise from 30 to 80% by weight of glycerol. These may be crude aqueous solutions, that are more or less dilute and that comprise more or less impurities, such as can be obtained from the methanolysis of vegetable oils.

The reactive solid is chosen from the catalysts suitable for carrying out the dehydration reaction of glycerol to acrolein and/or the oxydehydration reaction of glycerol to acrylic acid.

The fluidization may be provided by the vaporization of the glycerol solution, and/or by a stream of inert gas (nitrogen, $CO_2$, recycle gas, etc.), or air, oxygen, or a mixture of gases known to a person skilled in the art for optimizing the dehydration reaction of glycerol to acrolein and/or the oxydehydration reaction of glycerol to acrylic acid.

The temperature of the fluidized bed is generally between 180° C. and 400° C., preferably between 220° C. and 350° C., more particularly between 260° C. and 320° C.

The invention also relates to the use of a fluidized bed containing a reactive solid for simultaneously vaporizing and purifying an aqueous solution of glycerol, and carrying out the dehydration reaction of glycerol to acrolein and/or the oxydehydration reaction of glycerol to acrylic acid.

The invention also relates to a process for preparing acrolein and/or acrylic acid from glycerol in the gas phase in a fluidized bed reactor, characterized in that an aqueous solution of glycerol is sent directly into the fluidized bed containing a reactive solid maintained at a temperature between 180°

C. and 400° C., preferably between 220° C. and 350° C., in contact with which the dehydration reaction of glycerol to acrolein and/or the oxydehydration reaction of glycerol to acrylic acid is carried out.

Other features and advantages of the invention will emerge more clearly on reading the description which follows and with reference to the single appended FIGURE.

DETAILED DESCRIPTION OF PREFERRED EMBODIMENTS

The method according to the invention leads to high partial pressures of glycerol in the vapor phase, which has the advantage of vaporizing the glycerol and of making it react with a substantially higher productivity than that obtained with processes that carry out a vaporization prior to the reaction.

In the method according to the invention, the impurities present in the aqueous solution are removed simultaneously, as the fluidized bed technique makes it possible to continuously draw off a portion of the solid in order to regenerate it ex situ. Thus, the organic compounds present in the glycerol solution, but also the products resulting from the decomposition of the glycerol during this evaporation step, may result in the formation of coke which is deposited on the reactive solid. When the aqueous glycerol solution contains salts (for example sodium chloride or sodium sulfate), these salts are also deposited on the outer surface of the reactive solid during the evaporation of the aqueous glycerol solution. The reactive solid comprising the coke and/or the mineral salts may then be drawn off continuously in order to be regenerated in another reactor, before being sent back into the fluidized bed. The regeneration may also be carried out continuously in the reactor. The removal of the mineral salts may be carried out by simple washing of the solid with water, or any other suitable technique. It may also be carried out by continuous attrition of the catalyst, the salt deposit preferably being formed on the periphery of the catalyst grains. The regeneration of the solid consists of a combustion of the solid deposits, it is generally carried out with air in a reactor which may be, for example, another continuously operated fluidized bed, a circulating fluidized bed, a fixed bed, or any other reactor which may be suitable. Preferably, use will be made of a continuously operated fluidized bed. The combustion of the carbonaceous deposits on the reactive solid makes it possible not only to regenerate it but also to reheat it before returning it to the fluidized bed for evaporation/reaction of glycerol. This combustion may be carried out in the presence of a fuel, for example methane, which helps to bring the reactive solid to the temperature needed for the reactive evaporation of the aqueous glycerol solution.

Furthermore, in a fluidized bed, the particles are moving relative to one another which causes an attrition of the solid. In conventional fluidized beds, it is sought to limit this attrition which consumes solid and produces fine particles. In the process according to the invention, the attrition makes it possible to remove a portion of the deposits which are formed on the reactive solid. The fine particles thus formed by attrition are removed downstream, for example by separation in a cyclone and/or by filtration, or else by electrostatic precipitation.

As reactive solids in the method according to the invention, use may be made of homogeneous or multi-phase materials which have a Hammett acidity, denoted by $H_0$, of less than +2. As indicated in U.S. Pat. No. 5,387,720 which refers to the article by K. Tanabe et al. in "Studies in Surface Science and Catalysis", Vol. 51, 1989, chapters 1 and 2, the Hammett acidity is determined by amine titration using indicators or by adsorption of a gaseous base. The solids that correspond to the criterion of $H_0$ acidity of less than +2 may be chosen from natural or synthetic silaceous materials or acid zeolites; mineral carriers such as oxides, coated with mono-, di-, tri- or polyacidic inorganic acids; oxides or mixed oxides or else heteropolyacids.

Advantageously, the reactive solids are chosen from zeolites, Nafion® composites (based on sulfonic acid of fluoro polymers), chlorinated aluminas, phosphotungstic and/or silicotungstic acids and acid salts, and various solids of the metal oxide type such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups such as borate $BO_3$, sulfate $SO_4$, tungstate $WO_3$, phosphate $PO_4$, silicate $SiO_2$, or molybdate $MoO_3$.

The reactive solids may also be chosen from solids containing at least one element chosen from the list: Mo, V, W, Re, Cr, Mn, Fe, Co, Ni, Cu, Zn, Sn, Te, Sb, Bi, Pt, Pd, Ru and Rh, present in metallic form or in the oxide, mixed oxide, sulfate or phosphate form.

The solid used in the method of the invention must be not only a catalyst that makes it possible to carry out the dehydration of glycerol to acrolein and/or the oxydehydration reaction of glycerol to acrylic acid, but it must be strong in terms of mechanical strength and especially resistant to attrition in order to optimize its use in a fluidized bed.

Various methods known to a person skilled in the art may be used to form the reactive solid.

According to one embodiment of the process of the invention, the reactive solid is previously formed by spray drying. The catalyst may also be prepared from large particles which are ground until a particle size distribution is obtained that enables the catalyst to be used in a fluidized bed. However, this type of preparation method generally leads to catalysts that have insufficient mechanical strength, reducing the service life of the catalyst in the reactor, especially by wear via attrition of the catalyst grains.

According to one embodiment of the process of the invention, use is made of a catalyst prepared by mixing a suspension of precursors of the active material of the catalyst with a colloidal solution (binder), for example a solution of silica or alumina, followed by drying, via spray drying, of the suspension thus obtained, this method resulting in a powder composed of spherical particles that have a suitable particle size distribution for a fluidized bed application. However, this method of preparation requires binder contents in the vicinity of 50 wt %, which accordingly reduces the amount of active material in the final catalyst. Furthermore, during its use, the catalyst will undergo attrition which will modify the particle size distribution over time. This reduction of the particle size distribution will make it necessary to replace the catalyst before it is completely deactivated, in order to avoid hydrodynamic problems in the reactor.

According to one preferred embodiment of the process according to the invention, use is made, as a reactive solid, of a catalyst constituted of particles formed from a core of active material coated with a harder surface layer, for example a silica shell. There are several processes for obtaining this type of catalyst. A quick description is given in the publication by Krijn P. De Jong, CATTECH, June 1998, p. 87-95. Two methods are described therein: one, developed by Shell, consists in coating catalyst particles that are already formed with a silica shell and is described, for example, in documents WO 97/263131 and EP 697 247. The other method, initially developed by Du Pont, consists in mixing a suspension of active material with a colloidal solution of silica particles having a very small diameter, in general less than 7 nm, before carrying out a drying operation via spray drying. During the spray drying, the water evaporating therefrom is drawn off from the droplet, entraining the colloidal solution and giving rise to an enrichment of the surface, for example with silica. These two methods result in a catalyst that has a better resistance to attrition, and require a relatively low content of silica. It is preferred to use the coating method described by Shell, which makes it possible to easily regenerate the catalyst by addition of silica after embrittlement of the outer layer.

The use of catalysts that are enriched at the surface with binder such as silica, alumina or titanium oxide, thus having a harder surface layer than the material present in the core, has already been described for a certain number of applications, but has never been suggested for the dehydration reaction of glycerol to acrolein, or the oxydehydration of glycerol to acrylic acid. Mention may thus be made of U.S. Pat. No. 4,849,539 for the preparation of the acrylonitrile from propylene, U.S. Pat. No. 4,769,477 for the preparation of maleic anhydride by oxidation of butane, U.S. Pat. No. 4,677,084 and U.S. Pat. No. 6,107,238 for the general preparation of catalysts that are surface-enriched with silica, documents FR 2 826 959, U.S. Pat. No. 6,281,384, U.S. Pat. No. 6,437,193, U.S. Pat. No. 6,310,240 and WO 99/03809 for the oxidation of propylene to acrolein and/or acrylic acid, and of acrolein to acrylic acid.

One process for forming particles by spray drying a suspension of macroparticles and a colloidal solution of microparticles is also described in U.S. Pat. No. 4,477,492.

The catalyst constituted of particles formed from a core of active material coated with a surface layer enriched with binder such as silica, alumina or titanium oxide may also be obtained from two types of colloidal solutions of binder of different particle size, so as to keep some binder in the core of the particle while causing another fraction of binder to migrate to the surface. This type of process is especially illustrated in U.S. Pat. No. 5,302,566, U.S. Pat. No. 6,878,668 and U.S. Pat. No. 6,362,128. In general, polysilicic acid is used as a source of small-diameter colloidal silica.

One embodiment of the process according to the invention is represented in the single FIGURE: an aqueous solution of glycerol or of glycerin (4) is introduced into a reactor (1) containing a fluidized bed of a reactive solid. The fluidization may optionally be provided by a stream of inert gas (nitrogen, $CO_2$, recycle gas, etc.), or of air, of oxygen or of a mixture of gases known to a person skilled in the art for optimizing the dehydration reaction of glycerol to acrolein and/or oxydehydration reaction of glycerol to acrylic acid. The fluidized bed is heated via the heat exchanger (3). The glycerol/acrolein/acrylic acid vapors and water vapor are extracted from the reactor at (8) and a unit (7) makes it possible to recover the fine particles from the installation, and also, optionally, the salt that is deposited on the catalyst. A unit (6) makes it possible to wash the solid used in the fluidized bed in order to remove the mineral salts deposited. The reactor (2) is a regenerator of the reactive solid in which the solid drawn off from (1) is subjected to a combustion in the presence of a regeneration gas (5) containing molecular oxygen and/or fuels, the regenerated solid being sent back to the reactor (1). The gases resulting from the regeneration unit are discharged at (9).

The process according to the invention results in glycerol/acrolein/acrylic acid vapors and water vapor which are then subjected to absorption/purification steps according to techniques that are well known to a person skilled in the art. This process makes it possible to obtain acrolein and/or acrylic acid having minimized contents of by-products, such as hydroxyacetone, propanaldehyde or propionic acid, after the absorption step. It is known that the dehydration reaction of glycerol to acrolein generates secondary reactions that lead to the formation of hydroxyacetone or propanaldehyde, the latter possibly then being oxidized to propionic acid during the production of acrylic acid. The production of these by-products generally poses numerous separation problems and these impurities present greatly reduce the field of application of the acrolein and/or acrylic acid. It is therefore highly advantageous to minimize the content of impurities during the process in order to facilitate the final purification steps.

The invention also relates to the acrolein and/or acrylic acid obtained according to the process defined previously followed, in addition, by an absorption step, comprising a content of propanaldehyde, propionic acid and hydroxyacetone by-products such that the hydroxyacetone/acrolein molar ratio is less than 0.2, preferably less than 0.05, and the (propanaldehyde+propionic acid)/(acrolein+acrylic acid) molar ratio is less than 0.01, preferably less than 0.005. More particularly, it is possible to achieve a (propanaldehyde+propionic acid)/(acrolein+acrylic acid) molar ratio of less than 0.001, or even less than 0.0005.

The following examples illustrate the present invention without however limiting the scope thereof.

EXAMPLES

Catalyst Preparation

Example 1

Catalyst A of the Type $W/ZrO_2$—Si (with Polysilicic Acid)

Use is made of a tungstated zirconia powder from Dai-Ichi Kigenso KK (batch Z 1104), having a small particle size and the following characteristics:
% $WO_3$: 11.1%
Specific surface area ($m^2/g$): 69.9
$D_{50}$: 3.9 μm Preparation of Polysilicic Acid:
Sodium silicate is diluted so as to obtain a solution containing 6% of $SiO_2$
39.6 g of sodium silicate ($SiO_2.Na_2O$) containing 30.3% $SiO_2$
160.6 g of demineralized water
158.6 g of Dowex 650C resin are added in one go. The pH drops to around 3.5 and stabilizes.

The mixture is then filtered through a Büchner funnel and the filtrate (around 0.2 l) is stored in ice in order to prevent any gelling. The solution is preferably used in the hours following its preparation.

Preparation of the Suspension:
The suspension is obtained from the tungstated zirconia and from the polysilicic acid, which are mixed in the following proportions:
100.0 g of tungstated zirconia
166.9 g of 6% polysilicic acid
Approximately 7 g of sulfuric acid are added to the mixture so as to bring the pH to around 2.

The suspension is passed through a micronizer (rotational speed of the mill: 2500 rpm and that of the feed pump: 50 rpm). The particles of solid are reduced to micron size: $d_{50}$=3 μm, $d_{95}$=8 μm).

Spray Drying:
The spray-drying operation (Sodeva spray dryer) is carried out immediately after the preparations in order to avoid a problem of maturing of the solution. The drying gas is air. The spray nozzle relies on a principle of droplet generation by vibration from an ultrasound generator (ultrasound frequency: 20 kHz). The feed tank is kept stirring in ice. The operating conditions are:

T inlet: 220° C.
T outlet: 115-118° C.
Feed throughput: 0.130 kg/h on average
Air throughput: 4 m³/h The particle size distribution is analyzed after drying overnight in an oven at 80° C. The solid is then sieved so as to remove as many particles with a diameter of less than 50 μm as possible and also the particles greater than 160 μm.

Heat Treatment:

The heat treatment is carried out using a rotary furnace having a working capacity of around 500 ml. 50 g of solid are first treated at 300° C. under 60 l/h of nitrogen for 4 hours, then at 500° C. under nitrogen (60 l/h) for two hours. A final sieving is necessary in order to only retain the 50-160 μm fraction.

Example 2

Catalyst B of the Type W/ZrO₂—Si (by Silica Coating)

Use is made here of a batch of tungstated zirconia in the form of granules Z1044 Pellet. The granules are milled in order to only retain the fraction between 50 and 160 microns.

The tungstated zirconia powder is placed in a commercial fluidized bed coating machine (NIRO Aeromatic STREA-1), and fluidized with air at a temperature of 80° C. A colloidal solution of silica, LUDOX AS 40, containing 40 wt % of silica, is fed into the coater via a pump. The solution is sprayed using a nozzle with an air pressure of 1 bar. After addition of the solution, the fluidization is maintained for 30 minutes in order to dry the solid. The catalyst is recovered and calcined at 500° C. under a stream of nitrogen for 2 hours. The silica content of the final catalyst is 15 wt %, determined by the mass uptake of the tungstated zirconia.

Example 3

Catalyst X of the Type MoVTeNb (with Polysilicic Acid)

Preparation of the Dry Precursor:
Introduced into a Rayneri Trimix mixer are:
295 g of niobic acid (HY-340 CBMM, 81.5% Nb₂O₅)
660 g of oxalic acid dihydrate
5 liters of water It takes two hours for the niobic acid (Nb₂O₅ hydrate) to dissolve at 65° C. The molar ratio of the oxalic acid to the niobium is 3. The solution is collected and stored in order to be used in its entirety.

Next, a mixture of the following is prepared:
2819 g of ammonium heptamolybdate (Starck)
616 g of ammonium metavanadate (GFE)
802 g of telluric acid (H₆TeO₆, Fluka)
4061 g of demineralized water The solution is heated with stirring at 90-95° C. until dissolution is complete and a clear orange-red solution is obtained (approximately one hour including the heating time).

Finally, the solution of oxalic acid and niobic acid is introduced into the preceding solution. The mixture becomes cloudy and the color becomes orangey-yellow. After stirring for an additional half hour, the heating is halted. The suspension is then recovered and put into trays in a ventilated oven at 80° C. until complete evaporation (one night).

Preparation of Polysilicic Acid:
Sodium silicate is diluted so as to obtain a solution containing 6% of SiO₂:
396 g of sodium silicate (SiO₂.Na₂O) containing 30.3% SiO₂
1606 g of demineralized water
1586 g of Dowex 650C resin are added in one go. The pH drops to around 3.5 and stabilizes.

The mixture is then filtered through a Büchner funnel and the filtrate (around 2 l) is stored in ice in order to prevent any gelling. The solution is used in the hours following its preparation.

Preparation of the Suspension:
The suspension is obtained from the dry precursor and from the polysilicic acid, which are mixed in the following proportions:
1000 g of tellurium-based precursor
1669 g of 6% polysilicic acid Approximately 70 g of sulfuric acid are added to the mixture so as to bring the pH to around 2.

The suspension is passed through a micronizer (rotational speed of the mill: 2500 rpm and that of the feed pump: 50 rpm). The particles of solid are reduced to micron size: $d_{50}$=3 μm, $d_{95}$=8 μm.

Spray Drying:
The spray-drying operation is carried out as indicated in example 1 but with a feed throughput of 1.3 kg/h on average and an air throughput of 40 m³/h.

Heat Treatment:
The heat treatment is carried out using a rotary furnace having a working capacity of around 4385 ml. 513 g of solid are first treated at 300° C. under 60 l/h of air for 4 hours, then at 600° C. under nitrogen (60 l/h) for two hours. 410 g are recovered. A final sieving is necessary in order to only retain the 50-160 μm fraction: 370 g.

Example 4

Catalyst Y of the Type MoVSbNb (without Polysilicic Acid)

Step 1: Preparation of the Precursor:
Preparation of the Solution B:
The following are introduced into a Rayneri Trimix mixer:
295 g of niobic acid (HY-340 CBMM, 81.5% Nb₂O₅)
660 g of oxalic acid dihydrate (Prolabo)
5 liters of water It takes two hours for the niobic acid (Nb₂O₅ hydrate) to dissolve at 65° C. The molar ratio of the oxalic acid to the niobium is 3. The solution is collected and stored and will be used in its entirety.

Preparation of the Solution A:
3090 g of ammonium heptamolybdate (Starck)
615 g of ammonium metavanadate (GfE)
385 g of antimony oxide (Sb₂O₃, Campine)
9750 g of demineralized water The solution is heated with stirring at 99° C. for three hours after stabilization of the temperature. An opaque mixture with a dark blue color is obtained.

348 g of 30% aqueous hydrogen peroxide solution are added, so as to obtain a clear solution with an orange color.

2455 g of Ludox colloidal silica (Grace, AS-40) comprising 40 wt % of SiO₂ are added to the solution A without modifying the appearance of the mixture, which remains clear.

Formation of the Suspension:

The solution B of oxalic acid and of niobic acid is poured into the solution A/colloidal silica mixture. The mixture turns cloudy with the formation of a precipitate in suspension and the color becomes orangey yellow. Precursor fines (1370 g) originating from the preceding spray-drying operation are added to the solution at this stage. After stirring for an additional half hour, heating is halted. The suspension is then recovered and micronized. The d50 (mean diameter of the particles in suspension, measured by laser particle sizing on a Horiba LA300) changes from 18 µm to 0.2 µm with the micronization.

Micronization:

The micronization is carried out on a Labstar apparatus from Netzsch under the following operating conditions:
Mill speed: 3500 rpm
Feed pump indicator: 75 rpm
The outlet temperature of the product reaches 55° C.

The micronized suspension is immediately spray dried (solids content of the mixture, measured with an infrared dryer, at 33 wt %).

Spray Drying:

The spray-drying operation is carried out immediately after the micronization. A Niro Minor Mobile High-Tech spray dryer is used. The drying chamber has a jacket heightened by 2 m through which the steam passes. The drying gas is nitrogen. The spray nozzle is based on the principle of the generation of droplets by vibrations resulting from an ultrasound generator (Sodeva, ultrasound frequency: 20 kHz). The feed tank is kept stirred and the suspension is preheated to 60° C. using a thermostatically-controlled bath. The operating conditions are:
T° C. inlet: 210° C.
T° C. outlet: 105° C.
Feed throughput: 5.5 kg/h on average
Nitrogen throughput: 80 m³/h The size distribution of the particles is analyzed by laser particle sizing after drying overnight in an oven at 80° C. The solid is subsequently sieved so as to remove as many particles with a diameter of less than 50 µm as possible and also the particles of greater than 160 µm.

Step 2: Heat Treatments:

The heat treatment is carried out using a rotary furnace (200 mm in diameter, 270 mm cylinder length, working volume of 2.5 liters). One of the ends is closed. The gas is introduced using a pipe as far as the inside of the cylinder.

3319 g of solid are first treated at 310° C. [300-310] under 900 l/h [100-1200] of air for 4 hours and then at 600° C. under nitrogen (200 l/h) for two hours. The temperature ramp is 4.5° C./min in the solid, on average. An oxygen analyzer connected to the nitrogen supply system measures the oxygen content of the gas: typically between 1 and 2 ppm. The rotational speed of the furnace is 15 rpm.

2630 g are recovered. A final sieving is carried out in order to retain only the fraction from 50 to 160 µm: 2261 g.

The catalyst Y is composed of 6 batches resulting from analogous preparations and has the following characteristics:
Particle size measured by laser particle sizing on a Horiba LA300:
$D_{50}$=68 µm (mean diameter of the particles)
>160 µm=2 wt % (particles of more than 160 microns)<
<50 µm=10 wt % (particles of less than 50 microns)
Bulk density (measured by the method described in standard ISO 3923/1)=1.45 g/cm³.

Example 5

Catalyst Z of the Type MoVTeNb (without Polysilicic Acid)

Step 1: Preparation of the Dry Precursor:
Preparation of the Solution B:
The following are introduced into a Rayneri Trimix mixer:
295 g of niobic acid (HY-340 CBMM, 81.5% $Nb_2O_5$)
660 g of oxalic acid dihydrate (Prolab)
5 liters of water It takes two hours for the niobic acid ($Nb_2O_5$ hydrate) to dissolve at 65° C. The molar ratio of the oxalic acid to the niobium is 3. The solution is collected and stored in order to be used in its entirety.

Preparation of the Solution A:
2819 g of ammonium heptamolybdate (Starck)
616 g of ammonium metavanadate (GfE)
802 g of telluric acid ($H_5TeO_6$, Fluka)
4061 g of demineralized water [variation in the amount of water according to the preparations by a factor of 1 to 3; 4 l represents the lowest amount]

The solution is heated for one hour at 90-95° C. with stirring until dissolution is complete and a clear orange-red solution is obtained.

Addition of Colloidal Silica:

2655 g of Ludox colloidal silica (Grace, AS-40) comprising 40 wt % of $SiO_2$ are added to the solution A without modifying the appearance of the mixture, which remains clear.

Formation of the Suspension:

The solution B of oxalic acid and of niobic acid is poured into the solution A/colloidal silica mixture. The mixture turns cloudy with the formation of a precipitate in suspension and the color becomes orangey yellow. After stirring for an additional half hour, heating is halted. The suspension is then recovered and immediately spray dried (solids content of the mixture, measured using an infrared dryer, at 36 wt %).

Spray Drying:

The spray-drying operation is carried out immediately after the preparation of the suspension. The Niro Minor Mobile High-Tech spray dryer, modified internally, is preferably used. The drying gas is nitrogen. The drying chamber, heightened by 2 m, has a jacket through which steam passes. The spray nozzle is based on the principle of the generation of droplets by vibrations resulting from an ultrasound generator (Sodeva, ultrasound frequency: 20 kHz). The feed tank is kept stirred and the suspension is preheated to 60° C. using a thermostatically-controlled bath. The conventional operating conditions are:
T° C. inlet: 209-210° C.
T° C. outlet: 105-110° C.
Feed throughput: 5 kg/h on average
Nitrogen throughput: 80 m³/h The evaporative capacity of the spray dryer is 3 kg/h of water.

The solid recovered is subsequently further dried overnight in a ventilated oven at 80° C. The solid is subsequently sieved, so as to remove as many particles with a diameter of less than 50 µm as possible and also the particles of greater than 160 µm.

Step 2: Heat Treatments

The heat treatment is carried out using a rotary furnace (200 mm in diameter, 270 mm cylinder length, working volume of 2.5 liters). One of the ends is closed. The gas is introduced using a pipe as far as the inside of the cylinder. Various batches analogously treated were combined (air throughput 150 l/h (100 and 400 l/h), precalcination temperature 300° C., nitrogen throughput 150 or 200 l/h, calcination temperature 600° C., temperature gradient approximately 3.5 to 4.5° C./min).

2913 g of calcined solid were discharged after treating 3.805 kg of solid. A final sieving is necessary in order to retain only the 50-160 μm fraction.

This preparation was repeated several times in order to obtain 10 kg of catalyst, which were homogenized before use.

The catalyst Z is characterized by:
Final particle size distribution (but the pilot-plant team receives before charging):
  $D_{50}$ (mean diameter of the particles, measured using a Horiba LA300)=71 μm
  <50 μm (particles of less than 50 microns–fines)=15 wt %
  >160 μm (particles of more than 160 microns)=1 wt %
Bulk density (measured by the method described in standard ISO 3923/1): 1.40 g/cm$^3$.

Reactive Vaporization

Example 6

The catalysts prepared according to examples 1 to 5 are used in a fluidized bed, fed with an aqueous solution of glycerol at 50 wt % and maintained at 310° C. A dilute air stream provides the fluidization of the catalyst. The glycerol solution is directly vaporized in the fluidized bed. The total pressure in the reactor is 2.2 bar, with the following glycerol/water/$O_2$/$N_2$ molar ratios: 1/6/1/4, with a linear gas velocity of 10 cm/s. The products are collected at the outlet of the reactor and condensed in order to be analyzed by chromatography.

The results obtained appear in the table below:

| Catalyst | Glycerol conversion (%) | Acrolein yield (%) | Acrylic acid yield (%) |
|---|---|---|---|
| A | 100 | 20 | 1 |
| B | 100 | 10 | 1 |
| X | 55 | 2 | 3 |
| Y | 30 | 3 | 2 |
| Z | 35 | 1 | 2 |

Example 7

A tungstated zirconia catalyst (batch Z1044) from Dai Ichi Kigenso KK, obtained in the form of granules, was milled to a particle size of less than 315 microns. 150 g of this powder are sieved in order to select the fraction between 212 and 315 microns.

150 g of this solid catalyst were put into a fluidized bed. The fluidized bed consists of a stainless steel tube with a diameter of 41 mm and a total height of 790 mm. The fluidized bed is immersed in a fluidized sand bath, heated by electrical elements installed inside the bath. Three thermocouples recorded the temperature gradient along the tube. Air was supplied at a flow rate of 260 ml/min (standard conditions), and argon was supplied at a flow rate of 260 ml/min, underneath a porous metal plate that distributes the gas across the diameter of the reactor. A 20 wt % aqueous solution of glycerol prepared from crude glycerol having the following weight composition:

| Glycerol | 85% |
|---|---|
| NaCl | 4.5% |
| Water | 10% |
| Non-glycerin organic matter | 0.5% |
| Ash | <0.01% | is fed via a 7 mm metal tube that goes to the bottom of the bed, with a flow rate of 3 ml/min. The total pressure in the fluidized bed is 1 bar and the temperature is maintained at 350° C.

The experiment was carried out with this aqueous glycerol solution over a combined operating time of 24 hours, which corresponds to a combined total mass of 41 g of salt supplied at the inlet of the fluidized bed.

The products are collected at the outlet of the fluidized bed and condensed in order to be analyzed by liquid chromatography after stabilization with hydroquinone. 12% of the total flow is condensed in an ice trap (cooled with ice) filled with 800 ml of water.

The content of sodium in the product is measured by atomic absorption; and the result is expressed as a percentage of sodium initially present in the crude glycerol and is therefore expressed as the percentage of residual salt.

The results are given in the table below:

| | Combined operating time (h) | | | |
|---|---|---|---|---|
| | 15 | 18 | 21 | 24 |
| Amount of salt accumulated seen by the catalyst (g) | 25 | 30 | 36 | 41 |
| Acrolein yield (%) | 20 | 29 | 24 | 24 |
| Glycerol conversion (%) | 100 | 100 | 100 | 100 |
| Residual salt (%) | 0.12 | 0.09 | 0.10 | 0.10 |

After operating for more than 24 hours, the catalyst has seen more than 704 g of glycerol and 41 g of salt pass, and still results in an acrolein yield of almost 25% without visible deactivation. The process is capable of vaporizing the crude glycerol solution, by eliminating the salt and by converting the glycerol to acrolein.

The invention claimed is:

1. A process for preparing acrolein and/or acrylic acid from an aqueous solution of glycerol comprising:
  maintaining a fluidized bed comprising a reactive solid at a temperature ranging from 180° C. to 400° C.,
    wherein the reactive solid comprises a dehydration catalyst adapted to dehydrate the glycerol to acrolein and/or to oxydehydrate the glycerol to acrylic acid;
  injecting the aqueous glycerol solution directly into the fluidized bed to simultaneously vaporize the solution and react the glycerol on the reactive solid to produce the acrolein and/or acrylic acid; and
  purifying the acrolein and/or acrylic acid by absorption of by-products.

2. The process of claim 1, wherein the reactive solid comprises a homogeneous or multiphase material having a Hammett acidity of less than +2.

3. The process of claim 1, wherein the solid comprises zeolites; composites based on sulfonic acid of fluoro polymers; chlorinated aluminas; phosphotungstic and/or silicotungstic acids and acid salts; solids of the metal oxide type impregnated with acid functional groups including borate $BO_3$, sulfate $SO_4$, tungstate $WO_3$, phosphate $PO_4$, silicate $SiO_2$, or molybdate $MoO_3$; solids comprising at least one element comprising Mo, V, W, Re, Cr, Mn, Fe, Co, Ni, Cu, Zn, Sn, Te, Sb, Bi, Pt, Pd, Ru and Rh, present in metallic, oxide, mixed oxide, sulfate, or phosphate form; or mixtures thereof.

4. The process of claim 3, wherein said solids of the metal oxide type comprise tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$, silicoaluminate $SiO_2/Al_2O_3$, or mixtures thereof.

5. The process of claim 1, wherein said dehydration catalyst comprises particles comprising a core of active material coated with a binder-enriched surface layer.

6. The process of claim 1, wherein said aqueous solution of glycerol is simultaneously vaporized, purified, and converted to acrolein and/or acrylic acid.

7. The process of claim 6, wherein the dehydration catalyst comprises particles comprising a core of active material coated with a binder-enriched surface layer.

8. A process for preparing acrolein and/or acrylic acid from glycerol comprising:
  directly introducing an aqueous solution of glycerol into a fluidized bed comprising a reactive solid maintained at a temperature ranging from 180° C. to 400° C.,
  reacting said glycerol in a gas phase in contact with said reactive solid to form acrolein and/or acrylic acid and,
  purifying the acrolein and/or acrylic acid by absorption of by-products.

* * * * *

UNITED STATES PATENT AND TRADEMARK OFFICE
CERTIFICATE OF CORRECTION

PATENT NO.        : 8,530,697 B2                                     Page 1 of 1
APPLICATION NO. : 12/676782
DATED             : September 10, 2013
INVENTOR(S)       : Dubois et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 600 days.

Signed and Sealed this

Fifteenth Day of September, 2015

Michelle K. Lee
*Director of the United States Patent and Trademark Office*